United States Patent [19]

Gay

[11] 4,337,081
[45] Jun. 29, 1982

[54] 5-AMIDO-3-TRIHALOMETHYL-1,2,4-THIADIAZOLES AND THEIR USE AS HERBICIDES

[75] Inventor: Walter A. Gay, Cheshire, Conn.

[73] Assignee: Olin Corporation, New Haven, Conn.

[21] Appl. No.: 6,302

[22] Filed: Jan. 23, 1979

[51] Int. Cl.³ .................. A01N 43/82; C07D 285/08
[52] U.S. Cl. ........................................... 71/90; 71/73; 71/76; 548/128
[58] Field of Search .................... 260/306.8 D; 71/90, 71/73, 76

[56] References Cited

U.S. PATENT DOCUMENTS

| | | | |
|---|---|---|---|
| 3,260,725 | 7/1966 | Schroeder | 260/302 D |
| 3,324,141 | 6/1967 | Bernstein | 260/302 D |
| 3,573,317 | 3/1971 | Smith | 260/306.8 D |
| 3,629,275 | 12/1971 | Metzger et al. | 260/306.8 D |
| 3,673,203 | 6/1972 | Miller | 260/306.8 D |
| 3,720,684 | 3/1973 | Krenzer et al. | 260/306.8 D |
| 3,728,354 | 4/1973 | Rucker et al. | 260/306.8 D |
| 3,764,685 | 10/1973 | Krenzer et al. | 260/306.8 D |
| 3,873,299 | 3/1975 | Metzger et al. | 71/90 |
| 3,917,478 | 11/1975 | Moser et al. | 71/90 |
| 4,092,148 | 5/1978 | Cebalo | 71/90 |

*Primary Examiner*—Alton D. Rollins
*Attorney, Agent, or Firm*—William A. Simons; Thomas P. O'Day

[57] ABSTRACT

Disclosed are selected 5-amido-3-trihalomethyl-1,2,4-thiadiazole compounds of the formula:

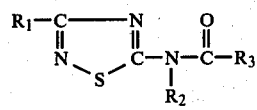

wherein $R_1$ is $CCl_3$ or $CF_3$; $R_2$ is hydrogen, a lower alkyl group of 1 to 4 carbon atoms or an aryl group having 6 to 8 carbon atoms; and $R_3$ is a lower alkyl group having from 2 to 4 carbon atoms, an aryl group having 6 to 8 carbon atoms, or $CX_3$, where X is H, Cl, F or $OCH_3$. These compounds are shown to have post-emergence herbicidal properties.

2 Claims, No Drawings

5-AMIDO-3-TRIHALOMETHYL-1,2,4-THIADIAZOLES AND THEIR USE AS HERBICIDES

BACKGROUND OF THE INVENTION

1. Field of the Invention

This invention relates to selected 5-amido-3-trihalomethyl-1,2,4-thiadiazoles and their use as post-emergence herbicides.

2. Description of the Prior Art

Various 3,5-substituted 1,2,4-thiadiazole compounds have been known to possess different types of pesticidal activity such as fungicidal, herbicidal, insecticidal, nematocidal and the like. For example, U.S. Pat. No. 3,629,275, which issued to Carl Metzger et al on Dec. 21, 1971, discloses the use of several carboxylic acid (1,2,4-thiadiazol-5-yl)-amides as herbicides. These disclosed amide compounds differ from the present inventive compounds by having a 3-position substituent selected from an alkyl group having 1-4 carbon atoms or a phenyl group.

Furthermore, various 1,3,4-thiadiazole compounds have also been known to possess different types of pesticidal activity. For example, U.S. Pat. Nos. 3,728,354 and 4,092,148, which issued to Dietrich Rucker et al and Tony Cebalo on Apr. 17, 1973, and May 30, 1978, disclose that certain amide derivatives of 1,3,4-thiadiazoles may be used as herbicides. However, it should be noted that 1,2,4-thiadiazoles and 1,3,4-thiadiazoles are treated as completely different classes of compounds by ordinarily skilled artisans in the pesticidal field because of their different modes of preparation, including the use of different starting materials.

BRIEF SUMMARY OF THE INVENTION

Accordingly, the present invention is directed to, as compositions of matter, selected 5-amido-3-trihalomethyl-1,2,4-thiadiazole compounds of the formula:

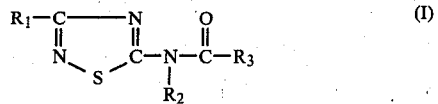

wherein $R_1$ is $CCl_3$ or $CF_3$; $R_2$ is hydrogen, a lower alkyl group of 1 to 4 carbon atoms or an aryl group having 6 to 8 carbon atoms; and $R_3$ is a lower alkyl group having 2 to 4 carbon atoms, an aryl group having 6 to 8 carbon atoms or $CX_3$, where X is H, Cl, F or $OCH_3$. The present invention also covers the use of these compounds as post-emergence herbicides.

DETAILED DESCRIPTION

The 5-amido compounds of the present invention may br prepared by reacting the corresponding 5-amine-3-trihalomethyl-1,2,4-thiadiazole with a desired acyl source such as an acid chloride or an acid anhydride. This general reaction is illustrated by the following Equation (A) wherein 5-amino-3-trichloromethyl-1,2,4-thiadiazole is reacted with trichloroacetyl chloride.

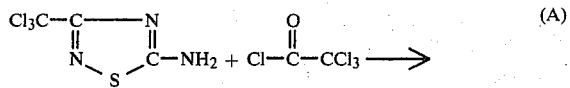

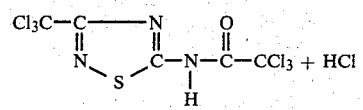

Suitable 5-amine-3-trihalomethyl-1,2,4-thiadiazole reactants include, besides 5-amino-3-trichloromethyl-1,2,4-thiadiazole mentioned above, 5-methylamino-3-trichloromethyl-1,2,4-thiadiazole, 5-anilino-3-trichloromethyl-1,2,4-thiadiazole, 5-amino-3-trifluoromethyl-1,2,4-thiadiazole. 5-Amino-3-trichloromethyl-1,2,4-thiadiazole is described in U.S. Pat. No. 3,260,725, issued to H. A. Schroeder on July 12, 1966, and is made by reacting 5-chloro-3-trichloromethyl-1,2,4-thiadiazole with ammonia. 5-Methyl-amino-3-trichloromethyl-1,2,4-thiadiazole is also described in this same U.S. Patent and is made by reacting methylamine with the same 5-chloro precursor. 5-Anilino-3-trichloromethyl-1,2,4-thiadiazole is described in U.S. Pat. No. 3,573,317 and is prepared by reacting 5-chloro-3-trichloromethyl-1,2,4-thiadiazole with aniline. 5-Amino-3-trifluoromethyl-1,2,4-thiadiazole is described in U.S. Pat. No. 3,917,478, which issued to Moser et al on Nov. 4, 1975, and is prepared by (1) the side-chain fluorination of 5-chloro-3-trichloromethyl-1,2,4-thiadiazole with a Swart's fluorination mixture consisting of antimony trifluoride, antimony trichloride and chlorine, followed by (2) the ammoniation of 5-chloro-3-trifluoromethyl-1,2,4-thiadiazole.

Suitable acid chlorides and acid anhydrides for use as reactants include trichloroacetyl chloride, acetyl chloride, benzoyl chloride and propionyl chloride and trifluoroacetic anhydride. Such acid chlorides and acid anhydrides are generally available commercially. Acid chlorides may be formed by reacting the corresponding acid with thionyl chloride. Acid anhydrides may be formed by reacting the corresponding acids with an acid chloride.

Any conventional reaction conditions may be employed in the synthesis of the present compounds and the present invention is not intended to be limited to any particular reaction conditions. Advantageously and preferably, the reaction is carried out with a molar excess of the acyl source (e.g., from about 0.5 to about 20 moles excess) and in the presence of a suitable inert solvent. Xylene is a preferred solvent, but other inert solvents may be used. The reaction temperature and time will both depend upon many factors including the specific reactants being used. In most situations, reaction temperatures from about 0° C. to about 150° C. and reaction times from about 1 hour to about 30 hours may be preferred. The product may be recovered from the reaction mixture by any conventional means, for example, distillation, extraction or simply by cooling the reaction mixture and removing the precipitated product by filtration. Finally, it should be noted that while the reaction illustrated by Equation (A) is a preferred method of preparing compounds of the present invention, other synthesis methods may also be employed.

In accordance with the present invention, it has been found that compounds of Formula (I), above, may be used for defoliation or for desiccation of the green parts of plants. They are, in particular, suitable singly, or in mixtures thereof, for the control of weeds. As contemplated herein, the term "weeds" is meant to include not only weeds in the narrow sense, by also in the broad sense, whereby to cover all plants and vegetation considered undesirable for the particular purposes in question. Whether the active compounds according to the present invention act as total or selective herbicides depends essentially on the amount applied, as the artisan will appreciate. Furthermore, it has been found that compounds of the present invention have shown activity as foliar fungicides and insecticides.

Specifically, in practicing the process of the present invention, undesirable plant and vegetation are contacted with a herbicidally effective amount of the above-mentioned compounds. It is to be understood that the term "herbicidally effective amount" as used in the specification and claims herein is intended to include any amount that will kill or control said undesirable plants and vegetation when either employed by itself (i.e., in full concentration) or in sufficient concentration with a carrier or other substance. Of course, this amount may be constantly changing because of the possible variations in many parameters. Some of these may include: the number and type of plants to be controlled or killed; the type of loci or media to which the present compounds can be applied (e.g., weeds within crop areas, fence lines); degree of effectiveness required; and type of carrier, if any. The step of contacting may be accomplished by applying the present active compounds to the undesirable plants themselves or to the immediate locus or ground surrounding said plants. In most situations, the application of the compounds of the present invention in amounts from about 0.1 pound per acre to about 10 pounds per acre will be sufficient for selective or total herbicidal effect.

The above-mentioned compounds of the present invention may be formulated and applied to any conventional methods that include using the compounds alone or with a carrier or other substances which may enhance the effectiveness of the chemical or facilitate handling. Moreover, the activity of the present compounds may be broadened by the addition thereto of other known biocides such as fungicides, other herbicides, insecticides and the like.

Specific methods of formulating and applying these active compounds include applying them in the form of dusts, dust or emulsion concentrates, wettable powders, and concentrates, granulates, dispersions, sprays, solutions and the like.

The dusts and dust concentrate are usually prepared by simply grinding together the active compounds of the present invention with a finely divided inert diluent such as walnut flour, diatomaceous earth, fullers earth, attaclay, talc or kaolin. Dusts generally contain from about 1% to about 15% by weight of active compound and dust concentrates usually contain from about 16% to about 75% by weight active compound. In practice, dust concentrates are usually admixed with more inert diluent at the site of use to form dusts before being applied to undesirable plant foliage.

Wettable powders are generally prepared in the same manner as dust concentrates, but usually about 1% to 10% by weight of a dispersing agent, for example, an alkali metal lignosulfonate and about 1% to about 10% of a surfactant, such as a non-ionic surfactant, are incorporated in the formulation. For most applications, the wettable powder is usually dispersed in water and applied as a spray.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application.

It is possible to formulate granulates whereby these active compounds are dissolved in an organic solvent and the resulting solution is then applied to a granulated mineral or the like (e.g.; bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one of the above-mentioned active compounds, or more than one active compound, is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that such herbicide formulations, the ingredients which may make up such formulations other than the active compounds and the dosages, and means of applying these formulations may include all known and conventional substances, amounts and means, respectively, that are suitable for obtaining the desired herbicidal result. And, therefore, such process parameters are not critical to the present invention.

The following examples further illustrate the present invention. All parts and percentages employed therein are by weight unless otherwise indicated.

EXAMPLE 1

5-Trichloroacetamido-3-Trichloromethyl-1,2,4-Thiadiazole

To a solution of 10.9 grams (0.05 mole) 5-amino-3-trichloromethyl-1,2,4-thiadiazole in 200 milliliters xylene at 110° C. was added 18.2 grams (0.1 mole) trichloroacetyl chloride over 0.5 hour. After heating for an additional 20 hours at 120° C., the low boiling materials were distilled in vacuo to leave 15.8 grams (87% yield) of pure product as residue; m.p. 157.7° C.

Analysis—Calculated for $C_4HCl_6N_3OS$: C, 16.50; H, 0.28; Cl, 58.46; N, 11.55; S, 8.81. Found: C, 16.56; H, 0.34, Cl, 58.42; N, 11.41; S, 8.62.

EXAMPLE 2

5-Trifluoroacetamido-3-Trichloromethyl-1,2,4-Thiadiazole

To a solution of 10.9 grams (0.05 mole) 5-amino-3-trichloromethyl-1,2,4-thiadiazole in 300 milliliters diethylether was added 10.5 grams (0.05 mole) trifluoroacetic anhydride over 15 minutes in a slight exothermic reaction to about 30° C. After standing at room temperature for 15 hours, the low boiling materials were distilled in vacuo. The semi-solid residue was heated with 100 milliliters hexane to remove the insoluble starting amine and the filtrate concentrated in vacuo to precipitate 8.0 grams (51% yield) of pure product; m.p. 115.8° C.

Analysis—Calculated for $C_5HCl_3F_3N_3OS$: C, 19.09; H, 0.32; Cl, 33.82; N, 13.36; S, 10.19. Found: C, 19.32; H, 0.55; Cl, 34.16; N, 13.57; and S, 10.16.

EXAMPLE 3

5-Chloroacetamido-3-Trichloromethyl-1,2,4-Thiadiazole

A solution of 10.9 grams (0.05 mole) 5-amino-3-trichloromethyl-1,2,4-thiadiazole and 11.3 grams (0.1 mole) chloroacetyl chloride in 200 milliliters xylene was refluxed at about 140° C. for 20 hours. Upon cooling the reaction mixture to −10° C., 10.7 grams (73% yield) pure product precipitated; m.p. 146.0° C.

Analysis—Calculated for $C_5H_3Cl_4N_3OS$: C, 20.36; H, 1.02; Cl, 48.07; N, 14.25; S, 10.87. Found: C, 20.44; H, 1.14; Cl, 48.35; N, 14.35; S, 10.18.

EXAMPLE 4

5-Acetamido-3-Trichloromethyl-1,2,4-Thiadiazole

A solution of 10.9 grams (0.05 mole) 5-amino-3-trichloromethyl-1,2,4-thiadiazole and 14.0 grams (0.18 mole) acetyl chloride in 200 milliliters xylene was refluxed at about 140° C. for 15 hours. The product precipitated (11.2 grams, 86% yield) after concentration in vacuo to approximately 50% of the original volume. A pure product of m.p. 193° C. was obtained by recrystallization from ethanol.

Analysis—Calculated for $C_5H_4Cl_3N_3OS$: C, 23.05; H, 1.55; Cl, 40.82; N, 16.13; S, 12.31. Found: C, 23.30; H, 1.80; Cl, 40.90; N, 16.41; S, 12.07.

EXAMPLE 5

5-Benzamido-3-Trichloromethyl-1,2,4-Thiadiazole

A solution of 10.9 grams (0.05 mole) 5-amino-3-trichloromethyl-1,2,4-thiadiazole and 14.1 grams (0.1 mole) benzoyl chloride in 200 milliliters xylene was refluxed at about 140° C. for 20 hours. Upon cooling the reaction mixture to −10° C., 13.7 grams (85% yield) pure product precipitated; m.p. 190.5° C.

Analysis—Calculated for $C_{10}H_6Cl_3N_3OS$: C, 37.23; H, 1.88; Cl, 32.97; N, 13.03; S, 9.94. Found: C, 37.42; H, 2.09; Cl, 32.72; N, 12.89; S, 9.94.

EXAMPLE 6

5-(N-Methyl-Trichloroacetamido)-3-Trichloromethyl-1,2,4-Thiadiazole

A solution of 5.8 grams (0.02 mole) 5-methylamino-3-trichloromethyl-1,2,4-thiadiazole and 9.0 grams (0.05 mole) trichloroacetyl chloride in 200 milliliters toluene was refluxed at about 110° C. for 20 hours. Upon cooling to −10° C., 2.7 grams pure product precipitated; m.p. 223° C. An additional 6.0 grams product was isolated by removal of the low boiling materials in vacuo. Total yield was 92%.

Analysis—Calculated for $C_6H_3Cl_6N_3OS$: C, 19.07; H, 0.80; Cl, 56.29; N, 11.12; S, 8.48. Found: C, 19.19; H, 1.03; Cl, 56.40; N, 11.24; S, 8.38.

EXAMPLE 7

5-(N-Phenyl-Trichloroacetamido)-3-Trichloromethyl-1,2,4-Thiadiazole

A solution of 14.7 grams (0.05 mole) 5-anilino-3-trichloromethyl-1,2,4-thiadiazole and 18.0 grams (0.1 mole) trichloroacetyl chloride in 200 milliliters toluene was refluxed at about 110° C. for 20 hours. After removal of the low boiling material in vacuo, the resulting residue was recrystallized from benzene to give 20.0 grams (91% yield) pure product; m.p. 158° C.

Analysis—Calculated for $C_{11}H_5Cl_6N_3OS$: C, 30.03; H, 1.15; Cl, 48.35; N, 9.55; S, 7.29. Found: C, 30.33; H, 1.25; Cl, 48.53; N, 9.60; S, 7.23.

EXAMPLE 8

5-Acetamido-3-Trifluoromethyl-1,2,4-Thiadiazole

A solution of 4.3 grams (0.05 mole) 5-amino-3-trifluoromethyl-1,2,4-thiadiazole and 7.0 grams (0.09 mole) acetyl chloride in 50 milliliters xylene was refluxed at about 140° C. for 20 hours. Upon cooling to room temperature 2.9 grams (55% yield) pure product precipitated; m.p. 178.1° C.

Analysis—Calculated for $C_5H_4F_3N_3OS$: C, 28.44; H, 1.91; N, 19.90; S, 15.18. Found: C, 28.67; H, 1.85; N, 19.98; S, 14.84.

EXAMPLE 9

5-Propionamido-3-Trichloromethyl-1,2,4-Thiadiazole

A solution of 21.8 grams (0.1 mole) 5-amino-3-trichloromethyl-1,2,4-thiadiazole and 18.5 grams (0.2 mole) propionyl chloride in 300 milliliters toluene was refluxed at about 110° C. for 14 hours. The product precipitated (18.4 grams, 91% yield) upon cooling to −15° C. and was isolated by filtration. A pure product of m.p. 150.0° C. was obtained by recrystallization from cyclohexane.

Analysis—Calculated for $C_6H_6Cl_3N_3OS$: C, 26.25; H, 2.20; Cl, 38.74; N, 15.30. Found: C, 26.37; H, 2.13; Cl, 38.86; N, 15.43.

HERBICIDE SCREEN

Some of the active materials made in the preceding examples were tested for activity as effective herbicides by the following method.

A uniform aqueous dispersion of each chemical was made by dissolving the chemical in a solution of acetone containing a nonionic surfactant in a concentration of 500 ppm. The resulting solution was diluted with water (1:9) to obtain a mixture of 10% acetone, 50 ppm surfactant, 0.208% by weight test candidate as shown in the following Tables, and the balance water; 50 ml. of this solution applied to a flat of 144 square inches corresponds to 10 lb/acre. If further dilutions were required for testing at lower concentrations, water was added to this stock solution and the surfactant maintained at 50 ppm.

The aqueous solutions containing each chemical were applied to flats seeded with representative monocotyledonous and dicotyledonous plants. The test chemical was applied to one such flat immediately after it was seeded (pre-emergence screening) and to the other flat after the first true plant leaves had developed (post-emergence screening). Response was rated 12 to 21 days after treatment on a scale of 0 to 10, where 0 represents no injury and 10 represents complete kill.

The crops and weeds used for the determination of activity were foxtail millet (*Setaria italica*), Japanese Millet (*Echinochloa crusgalli*), Crabgrass (*Digitaria sanguinalis*), Wild Oats (*Avena fatua*), Morning Glory (*Ipomoea purpurea*), Mustard (*Brassica nigra*), Pigweed (*Amaranthus retroflexus*), Sesbania (*Sesbania exaltata*), Velvet Leaf (*Abutilon Theophrasti*), Soybean (*Glycine max*), Cotton (*Gossypium hirsutum*), and Tomato (*Lycopersicon esculentum*).

The following Tables (I, II) illustrate the herbicidal activity claimed for the compounds of this invention. The 3 and 5-positions of the 1,2,4-thiadiazoles are occupied by the substituents as indicated. Table I shows the results of general testing at 10 lb./acre. The left side of each column shows the pre-emergence rating and the right side, the post-emergence rating. Table II shows the results of testing 3-trichloromethyl-5-trichloroacetamido-1,2,4-thiadiazole at 2.5, 1.2, and 0.6 lb./acre in the post-emergence screen only.

TABLE I

GENERAL HERBICIDE ACTIVITY* AT 10 LB./ACRE

| | | CROPS | | | | | | GRASSES | | | | | |
|---|---|---|---|---|---|---|---|---|---|---|---|---|---|
| 3-POS. | 5-POS. | SOYBEAN | | COTTON | | TOMATO | | FOXTAIL MILLET | | JAPANESE MILLET | | CRABGRASS | | WILD OATS | |
| $Cl_3C$ | $\underset{NHC-CCl_3}{\overset{O}{\parallel}}$ | 4F | 10 | 1 | 10 | 0 | 10 | 3S,F | 10 | 4S,F | 10 | 3S,F | 8 | 1 | 9S |
| $Cl_3C$ | $\underset{NHC-CF_3}{\overset{O}{\parallel}}$ | 0 | 3F | 0 | 2 | 0 | 3S | 0 | 4 | 0 | 1 | 3 | 0 | 0 | 4 |
| $Cl_3C$ | $\underset{NHC-CH_2Cl}{\overset{O}{\parallel}}$ | 0 | 3 | 0 | 1 | 0 | 3 | 0 | 6 | 0 | 1 | 4 | 2 | 0 | 3 |
| $Cl_3C$ | $\underset{NHC-CH_3}{\overset{O}{\parallel}}$ | 0 | 4 | 0 | 5 | 0 | 10 | 0 | 8 | 0 | 5 | 2 | 8 | 0 | 5 |
| $Cl_3C$ | $\underset{NHC-C_6H_5}{\overset{O}{\parallel}}$ | 0 | 3 | 0 | 3 | 0 | 10 | 0 | 5 | 0 | 0 | 0 | 2 | 0 | 5 |
| $Cl_3C$ | $\underset{\underset{CH_3}{\mid}}{\underset{NC-CCl_3}{\overset{O}{\parallel}}}$ | 0F | 5F | 0 | 2F | 0 | 2C,S | 0 | 9F | 0 | 0 | 3 | 2 | 0 | 1 |
| $Cl_3C$ | $\underset{\underset{C_6H_5}{\mid}}{\underset{NC-CCl_3}{\overset{O}{\parallel}}}$ | 0F | 5F | 0 | 3F | 0 | 1 | 0 | 8 | 0 | 2F | 5 | 0 | 0 | 1 |

| | | BROAD-LEAF WEEDS | | | | | | | | |
|---|---|---|---|---|---|---|---|---|---|---|
| 3-POS. | 5-POS. | MORNING GLORY | | MUSTARD | | PIGWEED | | SESBANIA | | VELVET LEAF | |
| $Cl_3C$ | $\underset{NHC-CCl_3}{\overset{O}{\parallel}}$ | 1 | 10 | 1 | 10 | 3S | 9 | 1 | 9S | 0 | 10 |
| $Cl_3C$ | $\underset{NHC-CF_3}{\overset{O}{\parallel}}$ | 0 | 3C | 0 | 0 | 6DO | 7 | 0 | 5 | 0 | 75 |
| $Cl_3C$ | $\underset{NHC-CH_2Cl}{\overset{O}{\parallel}}$ | 0 | 4 | 0 | 3 | 4DO | 5 | 0 | 9 | 0 | 8 |
| $Cl_3C$ | $\underset{NHC-CH_3}{\overset{O}{\parallel}}$ | 0 | 9 | 0 | 10 | 4DO | 10 | 0 | 10 | 0 | 8 |
| $Cl_3C$ | $\underset{NHC-C_6H_5}{\overset{O}{\parallel}}$ | 0 | 7 | 0 | 10 | 0 | 9 | 0 | 5 | 0 | 10 |
| $Cl_3C$ | $\underset{\underset{CH_3}{\mid}}{\underset{NC-CCl_3}{\overset{O}{\parallel}}}$ | 0 | 6F | 0 | 10 | 0 | 2 | 0 | 4 | 0 | 0 |
| $Cl_3C$ | $\underset{\underset{C_6H_5}{\mid}}{\underset{NC-CCl_3}{\overset{O}{\parallel}}}$ | 0 | 5F | 0 | 4 | 0 | 1 | 0 | 0 | 0 | 0 |

*F = Formative effects
S = Stunting
C = Chlorosis
DO = Damping Off

TABLE II

LOWER DOSAGE HERBICIDE* ACTIVITY FOR 3-$CCl_3$—5-$\underset{NHC-CCl_3}{\overset{O}{\parallel}}$—1,2,4-THIADIAZOLE

| | CROPS | | | GRASSES | | | | BROAD-LEAF WEEDS | | | | |
|---|---|---|---|---|---|---|---|---|---|---|---|---|
| | Soybean | Cotton | Tomato | Foxtail Millet | Japanese Millet | Crab-grass | Wild Oats | Morning Glory | Mustard | Pigweed | Sesbania | Velvet Leaf |
| 2.5 LB./ACRE | 9 | 9 | 10 | 10 | 8 | 10 | 6S | 10 | 9 | 10 | 9 | 9 |
| 1.2 LB./ACRE | 4C | 5C | 10 | 10 | 3 | 10 | 5S | 5 | 4 | 10 | 10 | 2 |

TABLE II-continued

LOWER DOSAGE HERBICIDE* ACTIVITY FOR 3-CCl$_3$—5-NH$\overset{\overset{\text{O}}{\|}}{\text{C}}$—CCl$_3$—1,2,4-THIADIAZOLE

| | CROPS | | | GRASSES | | | | BROAD-LEAF WEEDS | | | | |
|---|---|---|---|---|---|---|---|---|---|---|---|---|
| | Soybean | Cotton | Tomato | Foxtail Millet | Japanese Millet | Crab-grass | Wild Oats | Morning Glory | Mustard | Pigweed | Sesbania | Velvet Leaf |
| 0.6 LB./ACRE | — | 4C | 4C | 9 | 6 | 3 | 8 | 2 | 3 | 3 | 7 | 4 | 0 |

*Post-emergence

What is claimed is:

1. A method for controlling undesirable plant growth at a locus to be protected comprising applying to the locus a herbicidally effective amount of a compound of the formula:

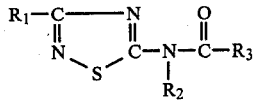

wherein $R_1$ is CCl$_3$ or CF$_3$; $R_2$ is phenyl; and $R_3$ is a lower alkyl group having 2 to 4 carbon atoms, a phenyl group or CX$_3$ where X is H, Cl or F.

2. The method of claim 1 wherein said compound has a formula of

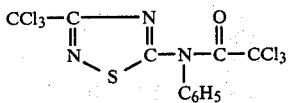

* * * * *